United States Patent
Maeda et al.

(10) Patent No.: US 11,087,050 B2
(45) Date of Patent: *Aug. 10, 2021

(54) GENERATION OF EVENT TRANSITION MODEL FROM EVENT RECORDS

(71) Applicant: INTERNATIONAL BUSINESS MACHINES CORPORATION, Armonk, NY (US)

(72) Inventors: Kumiko Maeda, Chuo-ku (JP); Yutaka Oishi, Kawasaki (JP); Chikafumi Yasumoto, Tokyo (JP); Jiayun Zhu, Tokyo (JP); Munetaka Ohtani, Fujisawa (JP); Yoshinori Tahara, Yamato (JP)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/416,814

(22) Filed: May 20, 2019

(65) Prior Publication Data

US 2019/0272352 A1    Sep. 5, 2019

Related U.S. Application Data

(63) Continuation of application No. 15/816,070, filed on Nov. 17, 2017.

(51) Int. Cl.
*G06F 30/20* (2020.01)
*G06F 17/18* (2006.01)
*G16H 10/60* (2018.01)
*G06Q 50/22* (2018.01)
*G06F 111/10* (2020.01)

(52) U.S. Cl.
CPC .......... *G06F 30/20* (2020.01); *G06F 17/18* (2013.01); *G16H 10/60* (2018.01); *G06F 2111/10* (2020.01); *G06Q 50/22* (2013.01)

(58) Field of Classification Search
CPC ...... G06F 30/20; G06F 17/18; G06F 2111/10; G06Q 50/22; G16H 15/00; G16H 10/60
See application file for complete search history.

(56) References Cited

U.S. PATENT DOCUMENTS

| 2004/0078232 A1* | 4/2004 | Troiani | G16H 50/20 |
| | | | 705/2 |
| 2013/0138459 A1* | 5/2013 | Barkan | G06F 19/00 |
| | | | 705/3 |

(Continued)

OTHER PUBLICATIONS

United States Patent Office Action for U.S. Appl. No. 15/816,070 dated Apr. 30, 2020 (21 pages).

(Continued)

*Primary Examiner* — Omar F Fernandez Rivas
*Assistant Examiner* — Michael Edward Cocchi
(74) *Attorney, Agent, or Firm* — Michael Best & Friedrich LLP (57) ABSTRACT

An event transition model for producing test data may be generated from a plurality of event records, each event record including an event time of an instance, wherein the event transition model includes a plurality of states, each state corresponding to one or more instances of the plurality of event records, event transition probabilities between states, and event transition interval times between states.

4 Claims, 8 Drawing Sheets

(56) References Cited

U.S. PATENT DOCUMENTS

| | | |
|---|---|---|
| 2015/0370992 A1* | 12/2015 | Yao ..................... G16H 50/50 703/2 |
| 2016/0085971 A1 | 3/2016 | Saxena et al. |
| 2016/0196297 A1* | 7/2016 | Almgren ................ G06F 16/93 707/649 |
| 2016/0253514 A1 | 9/2016 | Wu et al. |
| 2019/0034589 A1* | 1/2019 | Chen ..................... G06N 3/08 |
| 2019/0155968 A1 | 5/2019 | Maeda et al. |

OTHER PUBLICATIONS

United States Patent Office Examiner Interview Summary for U.S. Appl. No. 15/816,070 dated Jul. 31, 2020 (3 pages).
United States Patent Office Action for U.S. Appl. No. 15/816,070 dated Nov. 5, 2020 (23 pages).
United States Patent Office Advisory Action for U.S. Appl. No. 15/816,070 dated Feb. 9, 2021 (2 pages).
United States Patent Office Applicant-Initiated Interview for U.S. Appl. No. 15/816,070 dated Feb. 9, 2021 (2 pages).
United States Patent Office Notice of Allowance for U.S. Appl. No. 15/816,070 dated Apr. 2, 2021 (12 pages).

* cited by examiner

| Transitions | Count | Probabilities |
|---|---|---|
| T1: Initial⇒State 1 | 100 | 0.33 |
| T2: Initial⇒State 2 | 200 | 0.67 |
| T3: State 1⇒State 2 | ⋮ | ⋮ |
| T4: State 2⇒State 1 | ⋮ | ⋮ |
| T5: State 2⇒State 3 | | |
| T6: State 2⇒End | 170 | 0.23 |
| T7: State 3⇒End | 120 | 1 |

GENERATION OF EVENT TRANSITION MODEL FROM EVENT RECORDS

RELATED APPLICATIONS

This application is a continuation of U.S. patent application Ser. No. 15/816,070, filed Nov. 17, 2017, the entire content of which is incorporated by reference herein.

BACKGROUND

Technical Field

The present invention relates to the generation of an event transition model from event records.

Related Art

When constructing a data platform such as a cloud platform, it is necessary to evaluate the data platform with test data before the release. In order to improve the quality of the data platform, it is desirable to prepare a large amount of test data that is the same as or similar to actual data. However, an amount of available actual data for the test is limited for some reasons. On the other hand, randomly generated test data may cause a skew in training of the data platform.

SUMMARY

According to an aspect of the present invention, provided is a method, including generating an event transition model from a plurality of event records, each event record including an event time, wherein the event transition model includes a plurality of states corresponding to one or more instances of the plurality of event records, event transition probabilities between states, and event transition interval times between states.

The aspect may also include an apparatus performing the method, and a computer program product storing instructions embodied on a computer-readable medium or programmable circuitry, for causing a processor or the programmable circuitry to perform the method. The summary clause does not necessarily describe all features of the embodiments of the present invention. Embodiments of the present invention may also include sub-combinations of the features described above.

DETAILED DESCRIPTION

Hereinafter, example embodiments of the present invention will be described. The example embodiments shall not limit the invention according to the claims, and the combinations of the features described in the embodiments are not necessarily essential to the invention.

Figure 1:
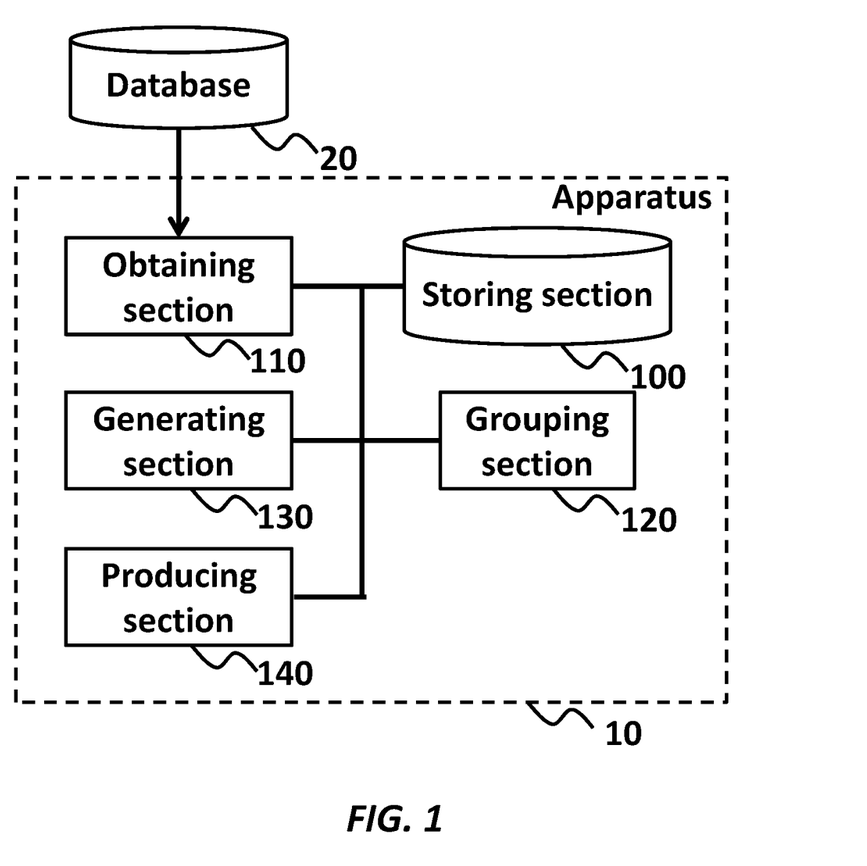
FIG. 1 shows an exemplary configuration of an apparatus 10, according to an embodiment of the present invention.

FIG. 1 shows an exemplary configuration of an apparatus 10, according to an embodiment of the present invention. The apparatus 10 may generate an event transition model from event records and produce test records from the event transition model.

The apparatus 10 may include a processor and/or programmable circuitry. The apparatus 10 may further include one or more computer readable mediums collectively including instructions. The instructions may be embodied on the computer readable medium and/or the programmable circuitry. The instructions, when executed by the processor or the programmable circuitry, may cause the processor or the programmable circuitry to operate as a plurality of operating sections.

Thereby, the apparatus 10 may be regarded as including a storing section 100, an obtaining section 110, a grouping section 120, a generating section 130, and a producing section 140.

The storing section 100 may store information used for the processing that the apparatus 10 performs. The storing section 100 may also store a variety of data/instructions used for operations of the apparatus 10. One or more other elements in the apparatus 10 (e.g., the obtaining section 110, the grouping section 120, the generating section 130, and the producing section 140) may communicate data directly or via the storing section 100, as necessary.

The storing section 100 may be implemented by a volatile or non-volatile memory of the apparatus 10. In some embodiments, the storing section 100 may store the event records, the event transition model, the test records, and other data related thereto.

The obtaining section 110 may obtain a plurality of event records. Each of the plurality of event records may include an ID, an instance of an event, and an event time of an instance at which the event has occurred. The obtaining section 110 may obtain the event records from the storing section 100 or an external database, such as a database 20. In an embodiment, the event record may be a medical record of a patient which may be generated by a medical doctor or medical device.

The grouping section 120 may classify the plurality of event records based on at least the IDs of the plurality of event records.

The generating section 130 may generate an event transition model from a plurality of event records. The event transition model may include a plurality of states. Each state of the plurality of states may correspond to one or more instances of the plurality of event records. The event transition model may further include event transition probabilities between two states, and event transition interval times between two states.

In an embodiment, the generating section 130 may generate the event transition model by recording, for each ID, an interval time between each pair of consecutive instances corresponding to event records.

The producing section 140 may produce at least one test record by generating an event based on at least the event transition model.

Figure 2:
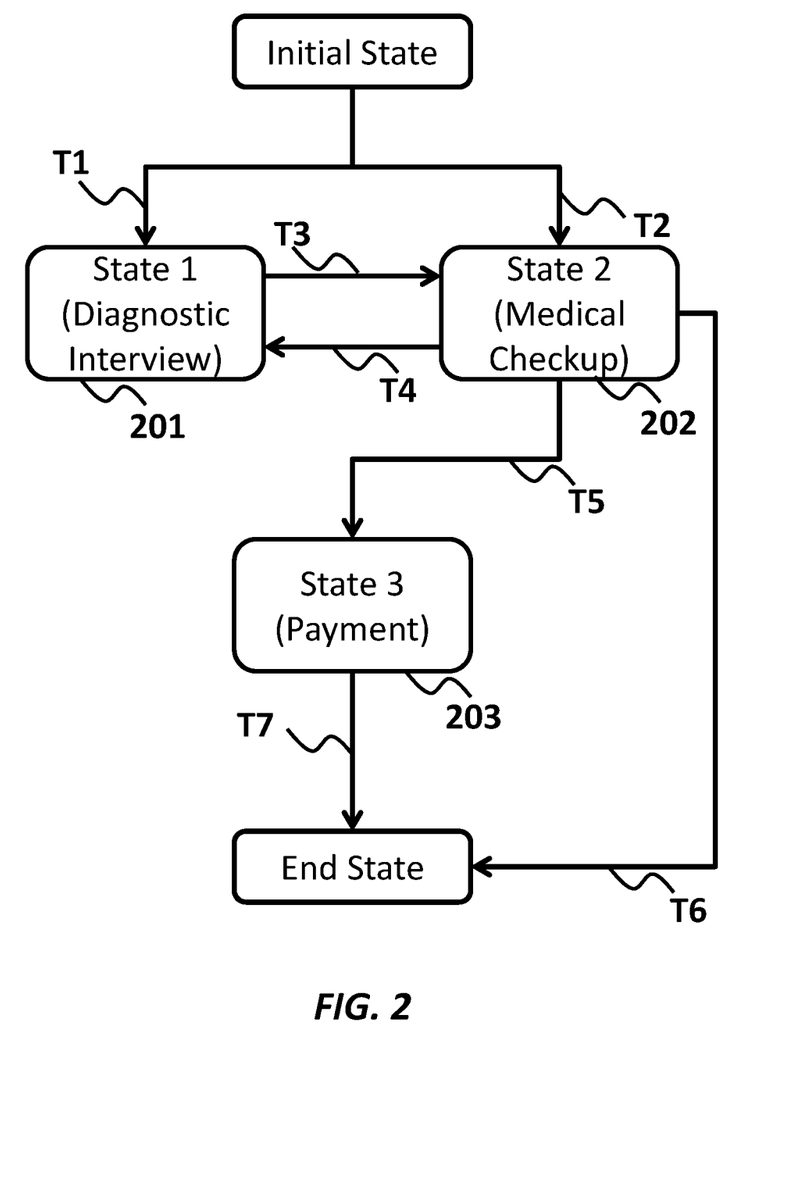
FIG. 2 shows an event transition model according to an embodiment of the present invention.

FIG. 2 shows an event transition model according to an embodiment of the present invention. The event transition model may be regarded as a state transition model. The event transition model includes Initial State, State 1, State 2, State 3, and End State. As shown in FIG. 2, State 1 corresponds to "Diagnostic Interview", State 2 corresponds to "Medical Checkup", and State 3 corresponds to "Payment."

In an embodiment, the generating section 130 may generate these states from the event record(s) including an instance "Diagnostic Interview", the event record(s) including an instance "Medical Checkup", and the event record(s) including an instance "Payment."

In the event transition model, Initial State may transit to State 1 (shown as "T1") or State 2 (shown as "T2"). State 1 may transit to State 2 (shown as "T3"). State 2 may transit to State 1 (shown as "T4"), State 3 (shown as "T5"), or End State (shown as "T6"). State 3 may transit to End State (shown as "T7"). In the embodiment of FIG. 2, the event transition model may include the event transition probabilities for T1-T7 and the event transition interval times for T1-T7.

Figure 3:
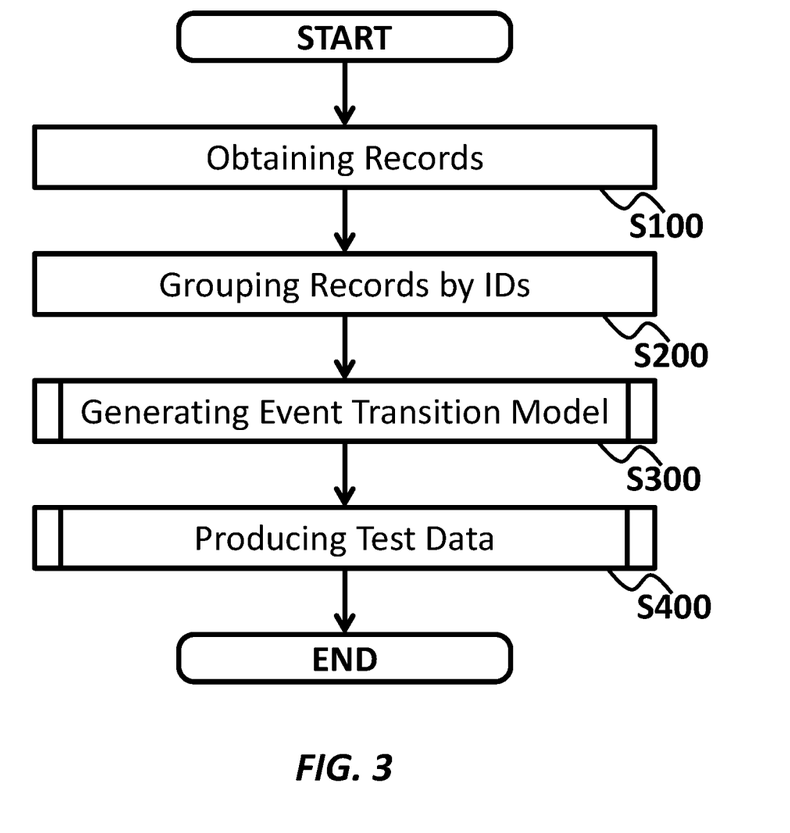
FIG. 3 shows an operational flow according to an embodiment of the present invention.

FIG. 3 shows an operational flow according to an embodiment of the present invention. The present embodiment describes an example in which an apparatus, such as the apparatus 10, performs operations from S100 to S400, as shown in FIG. 3.

At S100, an obtaining section, such as the obtaining section 110, may obtain a plurality of event records. Each event record may include at least an instance of an event and an event time.

The instance of an event may represent a type of an event that the event record represents. In an embodiment, the instance may be a type of a medical and/or clerical event of a patient occurring at a medical institution (e.g., a clinic, a hospital, and so on).

For example, the instance may include at least one of "Reception", "Diagnostic Interview", "Medical Checkup", "Medical Treatment", "Surgery", "Physiotherapy", "Payment", "Booking", and so on. In an embodiment, the instance may include further detailed types of events such as "Examination of Stomach", "Examination of Blood", "Examination of Brain", and so on.

The event time may relate to the time at which an event of the event record occurs. In an embodiment, the event time may include a time stamp recorded on the medical institution when the event has occurred.

Each event record may further include an ID of each event. The ID may be an ID of a patient associated with the event record, an ID of a medical institution associated with the event record, and so on, alone or in combination. In an embodiment, the ID of a patient may be an ID of the patient at a specific medical institution, or a common ID used at a plurality of medical institutions (e.g., EMPI: Enterprise Master Patient Index), and so on.

Each event record may further include one or more attributes relating to the event and/or the patient. In an embodiment, the one or more attributes may include at least one of biological information of the patient, information of the medical institution or device, and/or a result of an event (e.g., diagnostic image of an event including the instance "Medical Checkup").

The event record may be medical communication data made in accordance with a known protocol. In an embodiment, the event record may be medical communication data made in accordance with Health Level 7.

The obtaining section may obtain the medical records from a storing section, such as the storing section 100 and/or an external database such as the database 20. In an embodiment, the obtaining section may obtain medical record as the event records directly from a medical institution or a medical device.

At S200, a grouping section such as the grouping section 120 may classify the plurality of event records based on the IDs of the plurality of event records. In an embodiment, the grouping section may generate a plurality of groups, where each group includes one or more event records having a common ID. In an embodiment, the grouping section may allocate one group to event records having a common ID, or, to event records of both a common ID and a common date read from the event time.

At S300, a generating section such as the generating section 130 may generate an event transition model using the plurality of event records classified at S200. Details of the generations of the event transition model will be explained in relation to FIG. 4.

At S400, a producing section such as the producing section 140 may produce the one or more test records by generating an event based on at least the event transition model. Details of the generations of the event transition model will be explained in relation to FIG. 8.

Figure 4:
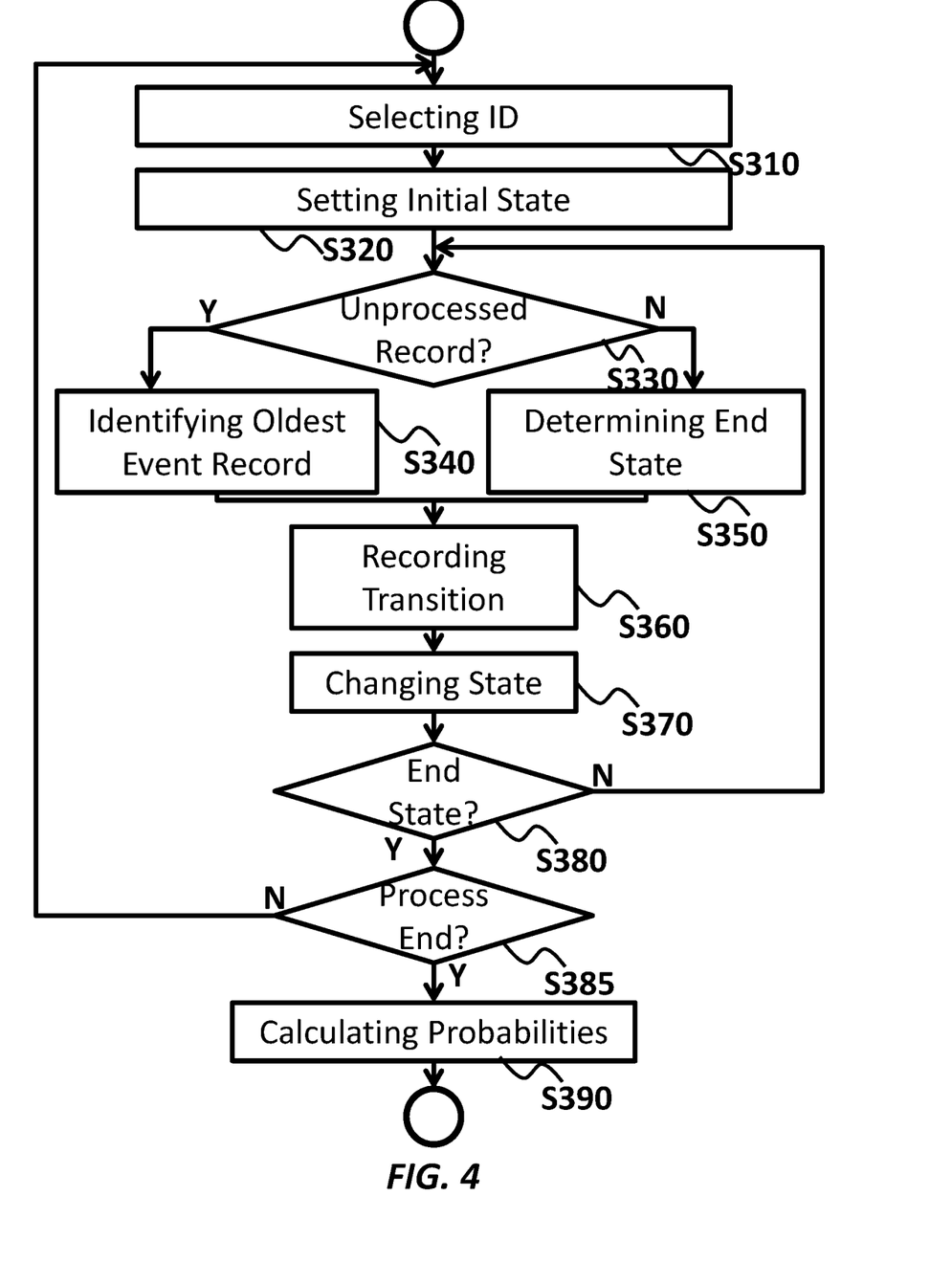
FIG. 4 shows a sub-flow of S300 according to an embodiment of the present invention.

FIG. 4 shows a sub-flow of S300 according to an embodiment of the present invention. Referring to FIG. 4, the generating section may perform the operations from S310 to S390 at S300 in FIG. 3.

At S310, the generating section may select an ID. In an embodiment, the generating section may select an ID that has not been selected at the previous S310. Hereinafter, the ID selected at the most recent S310 will be referred to as "target ID" for explanation. In an embodiment, the generating section may perform a process of S320-S380 for the target ID for each loop of S310-S385.

At S320, the generating section may set an initial state to a current state.

At S330, the generating section may determine whether there is an unprocessed event record left of the target ID. In an embodiment, the event records of the target ID may all be grouped into one group (which may be referred to as "target group") by the grouping section at S200. The generating section may determine whether there is an unprocessed record in the target group.

If determining that the unprocessed event record of the target ID exists, the generating section may proceed with an operation of S340, and if else, the generating section may proceed with an operation of S350.

At S340, the generating section may identify an oldest event record (which may be referred to as "target record") among unprocessed event records having the common ID of the target group. In an embodiment, the generating section may identify the instance of the target record as a subsequent state. For example, if the instance of the target record is "Diagnostic Interview", the generating section may determine "Diagnostic Interview" as the subsequent state.

At S350, the generating section may determine "End State" as a subsequent state.

At S360, the generating section may record a transition from the current state to the subsequent state. In an embodiment, the generating section may record a transition between the current state and the subsequent state, which corresponds to the instance of the oldest event. In the embodiment, the generating section may count up a number of a transition from the current state to the next state. For example, when the current state is set to "Initial State" at S320 and the subsequent state is determined as "Diagnostic Interview" at S340, the generating section may count up a number of transitions from the current state "Initial State" to the next state "Diagnostic Interview."

In an embodiment, the generating section may record the timestamp of the target record in association with the transition. In an embodiment, the generating section may further record, an interval time between the current state and the subsequent state. For example, the generating section may record an interval time between the timestamp of the previous target record and the timestamp of the target record, as the interval time between the current state and the subsequent state.

In a specific example, the generating section may record an interval time from the previous target record having an instance "Diagnostic Interview" to the target record having an instance "Medical Checkup", as one interval time between the current state "Diagnostic Interview" and the subsequent state "Medical Checkup." If there is no previous target record (e.g., a case when the current state is "Initial State"), then the generating section may record 0, a predetermined time, and/or a random time as the interval time, or may not record the interval time between the current state and the subsequent state.

In an embodiment, the generating section may record the transition with information of at least part of the one or more attributes in the target record in association with the transition.

At S370, the generating section may change the current state. In an embodiment, the generating section may set the subsequent state most recently determined at S340 or S350 as a new current state.

At S380, the generating section may determine whether the current state set at S370 is an "End State" or not. If the current state is an "End State", then the generating section may proceed with an operation of S385, and if not, then the generating section may go back to the operation of S330.

At S385, the generating section may determine whether to end the operations of S310-S380. In an embodiment, the generating section may determine whether all or a predetermined number of IDs have been selected at the operations of S310. If the all or the predetermined number of IDs have been selected, then the generating section may proceed with an operation of S390. And if unselected IDs remain, then the generating section may go back to the operation of S310 to select an unselected ID.

At S390, the generating section may generate the event transition model that includes the plurality of states, the event transition probabilities, and the event transition interval times according to the result of the operations of S360. The plurality of states may be the instances of the target records identified as the subsequent state at the operations of S340.

The generating section may calculate event transition probabilities from the number of transitions recorded at the operations of S360. In an embodiment, the generating section may calculate the event transition probability of a transition from a first state to a second state (e.g., "T1" in FIG. 2) as [the number of transition (e.g., "T1")]/[the number of transitions from the first state to all possible state(s)(e.g., "T1" and "T2")].

Figure 5:
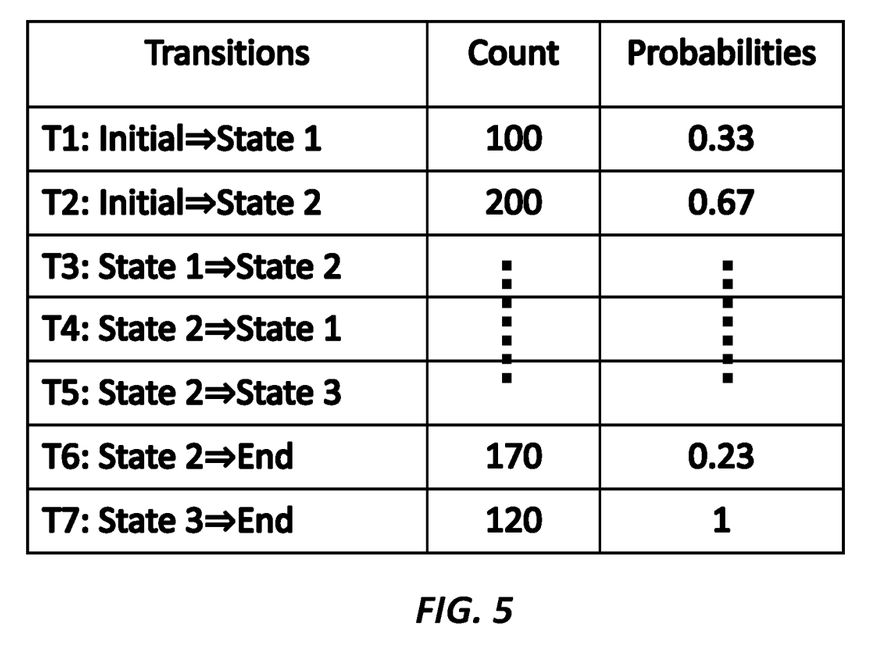
FIG. 5 shows a number of transitions between states according to an embodiment of the present invention.

FIG. 5 shows a number of transitions between states according to an embodiment of the present invention. The event transition model may include the number of transitions as shown in FIG. 5. The number of transitions may be generated by the generating section at the operations of S360 in FIG. 4.

FIG. 5 indicates that a number of transitions T1 from "Initial State" to "State 1" (e.g., "Diagnostic Interview") is 100, a number of transitions T2 from "Initial State" to "State 2" (e.g., "Medical Checkup") is 200, a number of transitions T6 from "State 2" to "End State" is 170, and a number of transitions T7 from "State 3" (e.g., "Payment") to "End State" is 120.

FIG. 5 also shows probabilities of the transitions between states according to an embodiment of the present invention. The event transition model may include the probabilities of transitions as shown in FIG. 5.

FIG. 5 indicates that a probability of the transition T1 is 0.33, which is calculated by (the number of T1)/[(the number of T1)+(the number of T2)], a probability of the transition T2 is 0.67, which is calculated by (the number of T2)/[(the number of T1)+(the number of T2)], a probability of the transition T6 is 0.23, which is calculated by (the number of T6)/[(the number of T4)+(the number of T5)+(the number of T6)], and a probability of the transition T7 is 1.

In an embodiment, the generating section may generate a conditional event transition probability. For example, the generating section may generate an event transition probability of the transition T1 that has occurred on AM of day from the number of the event records that have performed the transition T1 on AM according to the timestamps. For another example, the generating section may generate an event transition probability of the transition T1 of the event records having one or more specific values of the one or more attributes.

The event transition interval times may compose at least one interval time distribution of interval times between two states. The event transition interval times may compose a plurality of interval time distributions, each corresponding to a set of interval times between each possible pair of two states.

In an embodiment, each interval time in the at least one interval time distribution may correspond to two consecutive event records among the plurality of event records, which are recorded at operations of S340 in consecutive loops.

In another embodiment, the event transition interval times may be represented by parameters of at least one interval time distribution. For example, the generating section may calculate a mean and a variance of the at least one interval time distribution as the event transition interval times instead of the plurality of interval times. In the embodiment, the event transition interval times may comprise a mean and a variance of the at least one interval time distribution.

In an embodiment, the generating section may calculate correlations between the one or more attributes, and/or, the timestamps in the event records. In the embodiment, the event transition model may include information of the correlations of the attributes. The generating section may calculate the correlations using multiple linear regression analysis and/or principal component analysis.

Figure 6:
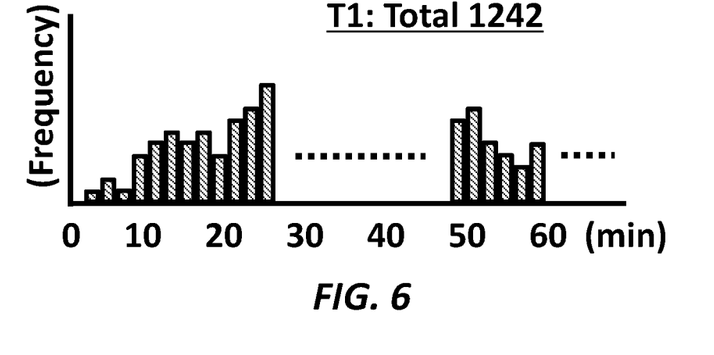
FIG. 6 shows a distribution of interval times of T1 according to an embodiment of the present invention.
Figure 7:
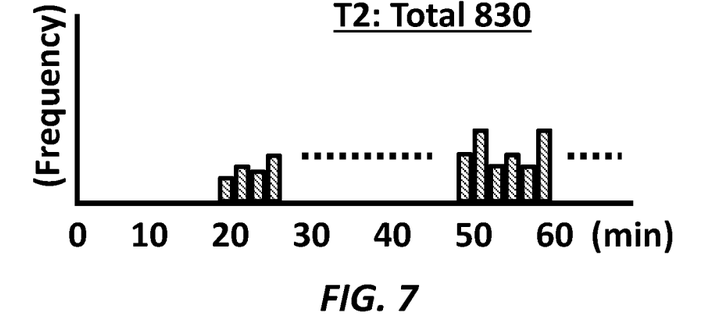
FIG. 7 shows a distribution of interval times of T2 according to an embodiment of the present invention.

FIGS. 6-7 show a distribution of interval times according to an embodiment of the present invention. The event transition model may include the distribution of interval times as shown in FIGS. 6-7. The interval times may be recorded at the operations of S360 and the distribution of interval times may be generated by the operation of S390 in FIG. 4.

FIG. 6 represents a distribution of the transition "T1" in FIG. 2, which is the transition from "Initial State" to "State 1." According to the distribution of FIG. 6, the number of transitions "T1" is 1242.

FIG. 7 represents a distribution of the transitions "T2" in FIG. 2, which is the transition from "Initial State" to "State 2." According to the distribution of FIG. 7, the number of the transitions "T2" is 830. In an embodiment, the event transition model may include a value of the frequency for each interval time range, instead of actual interval times between event records.

Figure 8:
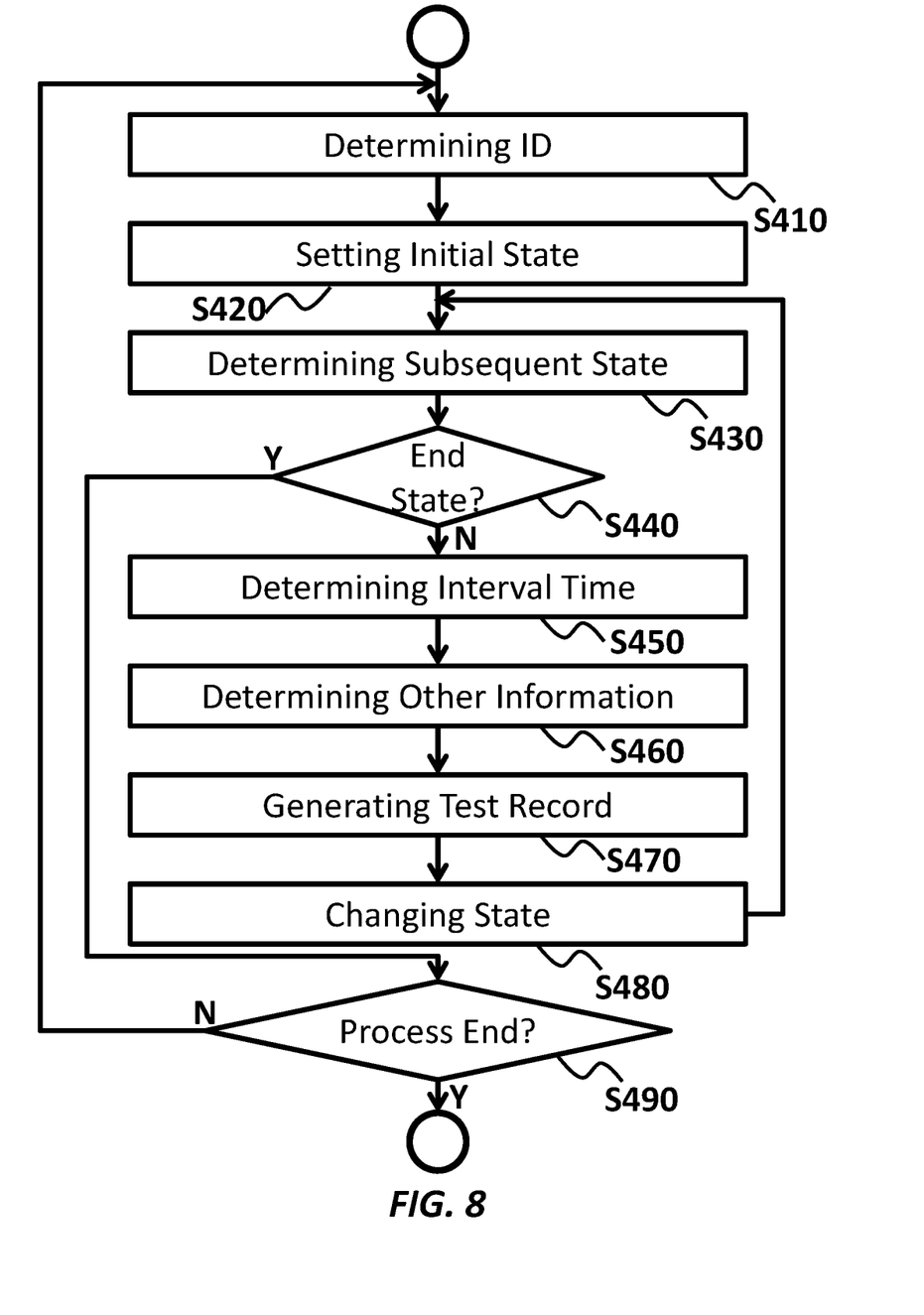
FIG. 8 shows a sub-flow of S400 according to an embodiment of the present invention.

FIG. 8 shows a sub-flow according to an embodiment of the present invention. Referring to FIG. 8, the section may perform the operations from S410 to S490 at S400 in FIG. 3.

At S410, the producing section may determine an ID. In an embodiment, the producing section may randomly determine an ID so as to obey a rule regulated for ID generation. For example, the producing section may determine the ID within a rule of Heath Level 7. Hereinafter, the ID determined at S410 may be referred to as "test ID."

At S420, the producing section may set an initial state to a current state for the test ID. The producing section may further set a random time stamp as a current time.

At S430, the producing section may determine a state of a subsequent event based on at least the event transition probabilities of the event transition model. The subsequent event corresponds to an event of a subsequent test record. In an embodiment, the producing section may randomly determine the state of the subsequent event from among a plurality of possible states with probabilities that each possible state will occur from the current state.

For example, in the event transition model of FIG. 2, it is possible that Initial State transits to State 1 "Diagnostic Interview" through T1 or State 2 "Medical Checkup" through T2. According to the embodiment of FIG. 5, the probability of the transition T1 is 0.33 and the probability of the transition T2 is 0.67. In the embodiment, the producing section may determine the transition T1 with a possibility of 0.33 and the transition T2 with a possibility of 0.67 when the current state is Initial State.

In some embodiments, the producing section may use the conditional event transition probabilities. In an embodiment, when there are one or more conditional event transition probability pairs and non-conditional event transitional probability pairs for the test ID, the producing section may use one conditional or non-transitional event transition probability pair that has the most significant difference.

For example, for the transition T1 and the transition T2 from Initial State, consider a case where the current time is during AM, a pair of probabilities of the transitions during AM of the day are $P_{AM}(T1)$ and $P_{AM}(T2)$, and a pair of probabilities of the transitions during any time of day are P(T1) and P(T2)). If $|P_{AM}(T1)-P_{AM}(T2)|>|P(T1)-P(T2)|$, then the producing section may use the pair of $P_{AM}(T1)$ and $P_{AM}(T2)$ to determine the transition from T1 and T2.

In an embodiment, the producing section may use the conditional event transition probabilities if a difference between conditions (e.g., $||P_{AM}(T1)-P_{AM}(T2)|-|P(T1)-P(T2)||$) is above a threshold.

At S440, the producing section may determine whether the state determined at S430 is an "End State" or not. If the determined state is an "End State", then the producing section may proceed with an operation of S490, and if not, then the producing section may proceed with an operation of S450.

At S450, the producing section may determine an interval time between a current event and the subsequent event based on the event transition interval times of the event transition model. The current event corresponds to an event of the last test record. In an embodiment, the producing section may randomly determine an interval time based on at least the interval time distribution.

For example, when the producing section may determine the transition T1 at S430, the producing section may determine the interval time based on the distribution shown in FIG. 6. On the other hand, when the producing section determines the transition T2 at S430, then the producing section may determine the interval time based on the distribution shown in FIG. 7.

At S460, the producing section may determine other information needed for the test record. In an embodiment, the producing section may randomly determine at least one attribute to include in the generated test record. The at least one attribute may be the same or similar to those included in the event record, and may include at least one of biological information of the patient, information of the medical institution or device, and/or a result of an event.

In an embodiment, the producing section may determine one or more attributes of a test record based on at least the correlations between the attributes. For example, the producing section may randomly determine some of the attributes of the test record, and then determine the rest of the attributes so as to reflect the correlation between the randomly determined attributes and the rest of the attributes. In an embodiment, the producing section may use the correlations only for one or more pairs of attributes that have a larger correlation than a threshold or have the top n correlations, where n is a predetermined integer.

In an embodiment, the producing section may determine the attributes of one test record by taking attributes of the other test record having the same test ID into consideration. In the embodiment, the producing section may determine the attributes of one test record so as to reflect the correlation between the attributes of one test record and the attributes of the other test record having the same test ID. For example, the producing section may determine the attributes of a current test record based on the attributes of the last test record.

In an embodiment, the producing section may determine the attributes of the test record based on common rules. For example, if a rule: A+B=C is common and attributes A and B are known, then the producing section may determine an attribute C by calculating A+B.

At S470, the producing section may generate a test record. The test record may include the state of the subsequent event determined at S430, as an instance.

The test record may further include a time stamp. The time stamp in the test record may correspond to the interval time between the current event and the subsequent event determined at S450. In an embodiment, the producing section may determine the time stamp by adding the interval time to the current time, and updating the current time with the determined time stamp. The test record may further include the other information determined at S460.

At S480, the producing section may change the current state. In an embodiment, the producing section may set the state of the subsequent event determined at S430 to the current state.

At S490, the producing section may determine whether to end the operations of FIG. 8. In an embodiment, the producing section may determine whether a predetermined number of the test records have been generated. If the decision is positive, then the producing section may end the operations of FIG. 8. And if not, then the producing section may go back to the operation of S410 to generate test records for another ID. For each ID, the producing section may iterate the operations of S430-S480, until event records for each state from an initial state to an end state are generated.

As explained above, the apparatus first generates the event transition model with the plurality of event records, and produces a necessary amount of test records that have close characteristics with the event records of the event transition model. In particular, the apparatus can maintain the temporal sequence of events appearing in test records consistent with the event records. Thereby, the apparatus may improve the quality of the data platform even when a number of event records available are limited.

Although the embodiments above have been explained mainly with examples of the medical records, the apparatus and methods may be applied for other fields. For example, in some embodiments of the present invention, the apparatus may generate an event transition model treating life events such as marriage, employment, retirement, childbearing, and/or disease, as the event record.

Figure 9:
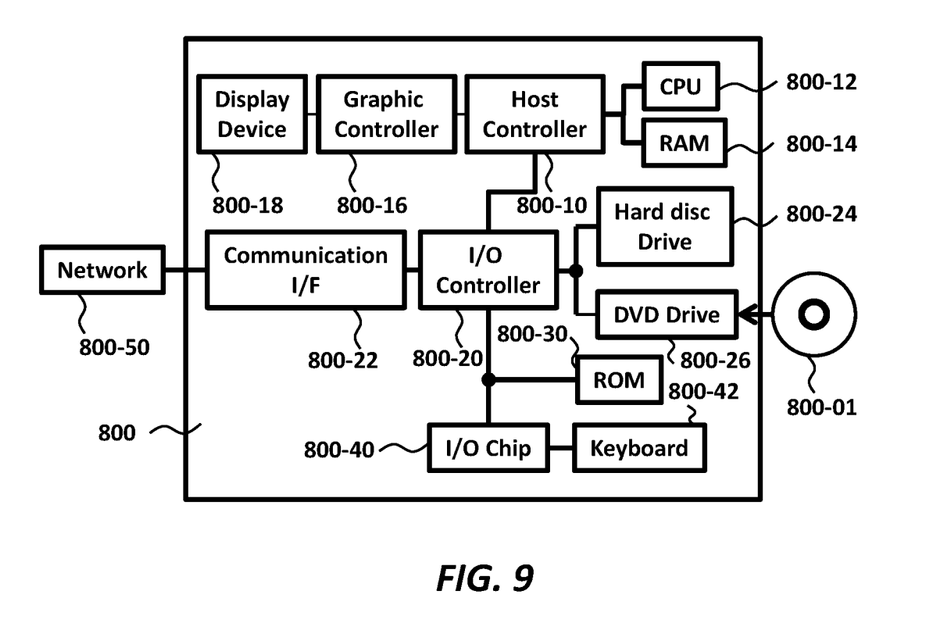
FIG. 9 shows an exemplary hardware configuration of a computer that functions as a system, according to an embodiment of the present invention.

FIG. 9 shows an exemplary hardware configuration of a computer configured for generating and utilizing the event transition model, according to an embodiment of the present invention. A program that is installed in the computer 800 can cause the computer 800 to function as or perform operations associated with apparatuses of the embodiments of the present invention or one or more sections (including modules, components, elements, etc.) thereof, and/or cause the computer 800 to perform processes of the embodiments of the present invention or steps thereof. Such a program may be executed by the CPU 800-12 to cause the computer 800 to perform certain operations associated with some or all of the blocks of flowcharts and block diagrams described herein.

The computer 800 according to the present embodiment includes a CPU 800-12, a RAM 800-14, a graphics controller 800-16, and a display device 800-18, which are mutually connected by a host controller 800-10. The computer 800 also includes input/output units such as a communication interface 800-22, a hard disk drive 800-24, a DVD-ROM drive 800-26 and an IC card drive, which are connected to the host controller 800-10 via an input/output controller 800-20. The computer also includes legacy input/output units such as a ROM 800-30 and a keyboard 800-42, which are connected to the input/output controller 800-20 through an input/output chip 800-40.

The CPU 800-12 operates according to programs stored in the ROM 800-30 and the RAM 800-14, thereby controlling each unit. The graphics controller 800-16 obtains image data generated by the CPU 800-12 on a frame buffer or the like provided in the RAM 800-14 or in itself, and causes the image data to be displayed on the display device 800-18.

The communication interface 800-22 communicates with other electronic devices via a network 800-50. The hard disk drive 800-24 stores programs and data used by the CPU 800-12 within the computer 800. The DVD-ROM drive 800-26 reads the programs or the data from the DVD-ROM 800-01, and provides the hard disk drive 800-24 with the programs or the data via the RAM 800-14. The IC card drive reads programs and data from an IC card, and/or writes programs and data into the IC card.

The ROM 800-30 stores therein a boot program or the like executed by the computer 800 at the time of activation, and/or a program depending on the hardware of the computer 800. The input/output chip 800-40 may also connect various input/output units via a parallel port, a serial port, a keyboard port, a mouse port, and the like to the input/output controller 800-20.

A program is provided by computer readable media such as the DVD-ROM 800-01 or the IC card. The program is read from the computer readable media, installed into the hard disk drive 800-24, RAM 800-14, or ROM 800-30, which are also examples of computer readable media, and executed by the CPU 800-12. The information processing described in these programs is read into the computer 800, resulting in cooperation between a program and the above-mentioned various types of hardware resources. An apparatus or method may be constituted by realizing the operation or processing of information in accordance with the usage of the computer 800.

For example, when communication is performed between the computer 800 and an external device, the CPU 800-12 may execute a communication program loaded onto the RAM 800-14 to instruct communication processing to the communication interface 800-22, based on the processing described in the communication program. The communication interface 800-22, under control of the CPU 800-12, reads transmission data stored on a transmission buffering region provided in a recording medium such as the RAM 800-14, the hard disk drive 800-24, the DVD-ROM 800-01, or the IC card, and transmits the read transmission data to network 800-50 or writes reception data received from network 800-50 to a reception buffering region or the like provided on the recording medium.

In addition, the CPU 800-12 may cause all or a necessary portion of a file or a database to be read into the RAM 800-14, the file or the database having been stored in an external recording medium such as the hard disk drive 800-24, the DVD-ROM drive 800-26 (DVD-ROM 800-01), the IC card, etc., and perform various types of processing on the data on the RAM 800-14. The CPU 800-12 may then write back the processed data to the external recording medium.

Various types of information, such as various types of programs, data, tables, and databases, may be stored in the recording medium to undergo information processing. The CPU 800-12 may perform various types of processing on the data read from the RAM 800-14, which includes various types of operations, processing of information, condition judging, conditional branch, unconditional branch, search/replace of information, etc., as described throughout this disclosure and designated by an instruction sequence of programs, and writes the result back to the RAM 800-14.

In addition, the CPU 800-12 may search for information in a file, a database, etc., in the recording medium. For example, when a plurality of entries, each having an attribute value of a first attribute is associated with an attribute value of a second attribute, are stored in the recording medium, the CPU 800-12 may search for an entry matching the condition whose attribute value of the first attribute is designated, from among the plurality of entries, and reads the attribute value of the second attribute stored in the entry, thereby obtaining the attribute value of the second attribute associated with the first attribute satisfying the predetermined condition.

The above-explained program or software modules may be stored in the computer readable media on or near the computer 800. In addition, a recording medium such as a hard disk or a RAM provided in a server system connected to a dedicated communication network or the Internet can be used as the computer readable media, thereby providing the program to the computer 800 via the network.

The present invention may be a system, a method, and/or a computer program product. The computer program product may include a computer readable storage medium (or media) having computer readable program instructions thereon for causing a processor to carry out aspects of the present invention. The apparatus of the embodiments of the present invention may include the computer readable medium and the processor or programmable circuitry operable to execute the instructions.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to individualize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

As made clear from the above, the embodiments of the present invention enable to generate the event transition model from the event records and produce the test records.

What is claimed is:

1. A method, comprising:
    collecting, over a network via a network communication interface from one or more electronic devices associated with a medical institution, a plurality of authentic event records, each authentic event record including an identifier, event type information of a medical or clerical event related to the medical institution, and a timestamp corresponding to a time the medical or clerical event occurred;
    recording an authentic transition between each pair of consecutively occurring events in the collected plurality of authentic event records including the same identifier;
    recording an authentic interval time between each recorded authentic transition;
    generating and recording, for each type of transition in the recorded authentic transitions, a number of times the type of transition occurred;
    generating and recording, for each type of transition in the recorded authentic transitions, a probability the type of transition will occur based on the number of times the type of transition occurred in the recorded authentic transitions;
    generating and recording, for each type of transition in the recorded authentic transitions, an interval time distribution based on the recorded interval times for the type of transition;
    generating and recording a first synthetic test record for testing a data platform of the medical institution, the first synthetic test record including first synthetic event type information corresponding to a first synthetic event and a first synthetic timestamp;
    generating a synthetic transition from the first synthetic event to a second synthetic event using the recorded probabilities of transitions from the recorded authentic transitions starting with the first synthetic event;
    generating a subsequent, second synthetic test record for testing the data platform of the medical institution, the second synthetic test record including second synthetic event type information corresponding to the second synthetic event and a second synthetic timestamp, wherein the second synthetic time stamp of the second synthetic test record is set based on the first synthetic timestamp of the first synthetic event and a synthetic interval time, wherein the synthetic interval time is set based on the interval time distribution generated for the synthetic transition, wherein the interval time distribution is generated using the recorded interval times for the type of transition of the authentic event records for the synthetic transition; and
    testing the data platform of the medical institution using the generated one or more new synthetic test records.

2. The method of claim 1, wherein the event transition interval time distributions include at least one of a mean and a variance of the recorded interval times for each type of transition.

3. The method of claim 1, wherein the generating of the first synthetic test record includes:
    setting the first synthetic event to an initial event of a plurality of events, and
    iterating, until synthetic test records for each event from the initial event to an end event of the plurality of events are generated.

4. The method of claim 3, wherein determining at least one attribute to include in the generated second synthetic test record, and the at least one attribute includes at least one selected from a group consisting of: biological information of a patient, information of the medical institution, information of the one or more electronic devices associated with the medical institution, a result of the medical or clerical event, and a diagnostic image.

* * * * *